(12) United States Patent
Decock et al.

(10) Patent No.: US 12,053,414 B2
(45) Date of Patent: Aug. 6, 2024

(54) DEVICE FOR ASSISTING WITH THE USE OF A DEVICE FOR DISPENSING A LIQUID PRODUCT

(71) Applicant: Nemera La Verpillière, La Verpilliere (FR)

(72) Inventors: Thierry Decock, Lyons (FR); Loïck Cassagne, Saint-Alban-de-Roche (FR); Pierre Pintus, Crachier (FR)

(73) Assignee: NEMERA LA VERPILLIÉRE, La Verpillière (FR)

( * ) Notice: Subject to any disclaimer, the term of this patent is extended or adjusted under 35 U.S.C. 154(b) by 944 days.

(21) Appl. No.: 16/968,015

(22) PCT Filed: Feb. 5, 2019

(86) PCT No.: PCT/EP2019/052777
§ 371 (c)(1),
(2) Date: Dec. 23, 2020

(87) PCT Pub. No.: WO2019/154807
PCT Pub. Date: Aug. 15, 2019

(65) Prior Publication Data
US 2021/0113372 A1    Apr. 22, 2021

(30) Foreign Application Priority Data
Feb. 6, 2018 (FR) ...................................... 1850987

(51) Int. Cl.
*A61F 9/00* (2006.01)
*A61M 31/00* (2006.01)
*A61M 35/00* (2006.01)
*G01C 9/02* (2006.01)
(Continued)

(52) U.S. Cl.
CPC ........... *A61F 9/0008* (2013.01); *A61M 31/00* (2013.01); *A61M 35/003* (2013.01); *G01C 9/02* (2013.01);
(Continued)

(58) Field of Classification Search
None
See application file for complete search history.

(56) References Cited

U.S. PATENT DOCUMENTS

| 4,820,281 A | 4/1989 | Lawler, Jr. |
| 2003/0045840 A1 | 3/2003 | Burko |

(Continued)

FOREIGN PATENT DOCUMENTS

| CN | 1383797 A | 12/2002 |
| CN | 1551786 A | 12/2004 |

(Continued)

OTHER PUBLICATIONS

JP4396222_translation (Year: 2010).*
(Continued)

*Primary Examiner* — Manuel A Mendez
(74) *Attorney, Agent, or Firm* — Jonathan A. Winter; Farber LLC

(57) ABSTRACT

An assistance device for assisting with the use of a device for dispensing a liquid product in the form of drops having a tank including a connector for rigid connection to the dispensing device, an optical device arranged near a dispensing orifice, configured to provide information on the dispensing of a liquid drop by the dispensing device, a measuring device for measuring the inclination, configured to provide information on the inclination of the dispensing device connected to the assistance device, and a system for processing information on the dispensing of a drop and on the inclination of the dispensing device connected to the assistance device to provide information on the amount of liquid product dispensed. The invention also relates to a dispensing kit and a method for determining the amount of liquid product dispensed in the form of drops by a liquid-dispensing device, with the assistance device.

18 Claims, 4 Drawing Sheets

(51) Int. Cl.
*G01F 22/00* (2006.01)
*G01L 1/22* (2006.01)

(52) U.S. Cl.
CPC ............... *G01F 22/00* (2013.01); *G01L 1/22* (2013.01); *A61M 2205/3306* (2013.01); *A61M 2205/332* (2013.01); *A61M 2205/3327* (2013.01); *A61M 2205/3379* (2013.01)

(56) References Cited

U.S. PATENT DOCUMENTS

| | | | |
|---|---|---|---|
| 2012/0028361 | A1 | 2/2012 | Kathe et al. |
| 2014/0257206 | A1 | 9/2014 | Fateh |
| 2014/0283620 | A1 | 9/2014 | Kolko et al. |
| 2015/0289805 | A1 | 10/2015 | Eaton et al. |

FOREIGN PATENT DOCUMENTS

| | | | |
|---|---|---|---|
| CN | 101513946 | A | 8/2009 |
| CN | 102362180 | A | 2/2012 |
| CN | 105163777 | A | 12/2015 |
| DE | 202016003139 | U1 | 6/2016 |
| JP | H565335 | U | 8/1993 |
| JP | 2005131887 | A | 5/2005 |
| JP | 2005140514 | A | 6/2005 |
| JP | 4396222 | B2 * | 1/2010 |
| JP | 2010145334 | A | 7/2010 |
| WO | 2009148345 | A2 | 12/2009 |
| WO | 2011137900 | A2 | 11/2011 |
| WO | 2014052137 | A1 | 4/2014 |
| WO | 2016123553 | A1 | 8/2016 |
| WO | 2017205824 | A1 | 11/2017 |

OTHER PUBLICATIONS

Decision of Refusal from Japanese Patent Office for Application No. 2020-542283 dated Jul. 25, 2023 (English Translation only).
European Office Action (Article 94(3)); EP Application No. 19705134.5; Apr. 26, 2024.

* cited by examiner

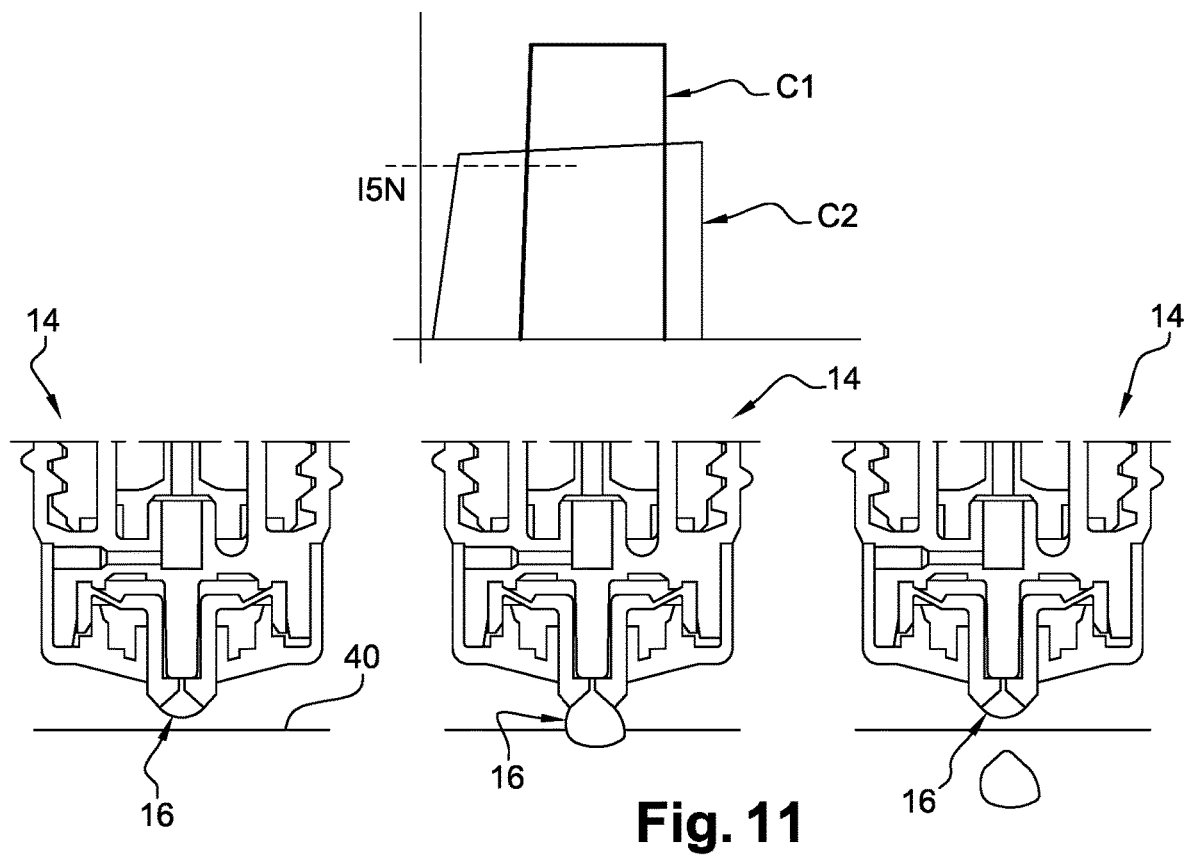
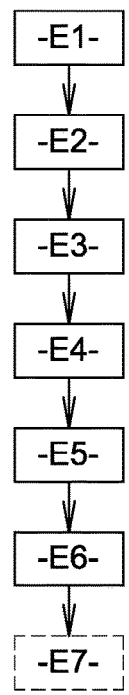
Fig. 10
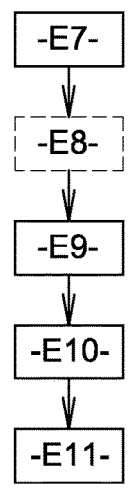
Fig. 12
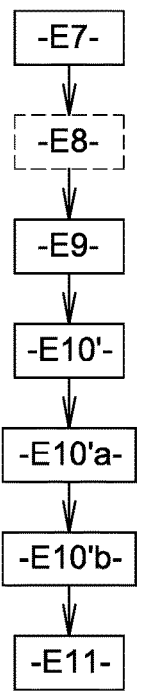
Fig. 13

DEVICE FOR ASSISTING WITH THE USE OF A DEVICE FOR DISPENSING A LIQUID PRODUCT

FIELD OF THE INVENTION

The invention relates to an assistance device for assisting with the use of a device for dispensing a liquid product in the form of drops.

BACKGROUND OF THE INVENTION

When a liquid product is dispensed, it is often interesting to know the amount of liquid dispensed. This is particularly true for the administration of medical products, for which the amount of medication administered must be precisely controlled according to the prescription. An underdose or overdose of medication must be avoided to preserve the patient's health.

US 2014/0257206 describes a device for controlling the instillation of drops of ophthalmic liquid comprising an optical drop counter. The device can detect the presence of a drop at the outlet of a bottle of medication and thus count the number of drops dispensed. The device and/or the user can therefore control the number of drops administered. However, this device does not provide any information on the amount of liquid product dispensed. The volume of a drop is in fact not always constant. It depends on numerous parameters which vary depending on the conditions under which each drop is dispensed.

The invention aims in particular to provide a device for determining the amount of liquid product dispensed.

SUMMARY OF THE INVENTION

Thus, the invention relates to an assistance device for assisting with the use of a device for dispensing a liquid product in the form of drops comprising a tank, the assistance device comprising:
  means for rigid connection to the dispensing device,
  optical means intended to be arranged near an orifice for dispensing liquid product, configured to provide information on the dispensing of a drop of the liquid product by the dispensing device,
  means for measuring the inclination, configured to provide information on the inclination of the dispensing device connected to the assistance device, and
  a system for processing information on the dispensing of a drop and on the inclination of the dispensing device connected to the assistance device in order to provide information on the amount of liquid product dispensed.

Numerous experiments and studies have revealed that the inclination of the dispensing device at the time of dispensing a drop affects the volume of the drop, which means that by taking a measurement of the inclination, the volume of a drop can be estimated after processing this information. Thus, the proposed assistance device comprises means for measuring the inclination of the dispensing device to which it is connected and an information processing system, and is therefore able to provide relevant information which can then be used to estimate a volume of the dispensed drop and therefore the amount of liquid product dispensed. In addition, it comprises optical means for detecting the presence of a drop near the dispensing orifice, in order to obtain information on the dispensing of a drop of the liquid product by the dispensing device, which can then be used by the information processing system to process the information on the dispensing of a drop in relation to the inclination of the dispensing device at the time of dispensing the drop. The assistance device thus designed can determine a numerical value of the amount of liquid product dispensed.

Furthermore, knowing the amount of liquid product dispensed, the information processing system can advantageously deduce the amount of liquid product remaining in the tank of the dispensing device. This amount can then be converted into a theoretical number of remaining drops, based on theoretical conditions of use of the dispensing device. This information is likely to be of interest to users, allowing them to anticipate the time when the tank will be empty and therefore to assess the autonomy of use. It can also be used for other types of analysis or processing to obtain additional information.

Note that the information processing may take into account other information provided to the information processing system to estimate the amount of liquid dispensed, for example information on the physical or chemical properties of the liquid product, the valve geometry, tables of predefined values.

"Optical" means any electromagnetic wave, belonging to the visible or non-visible spectrum. The optical means are generally means capable of transmitting, receiving and/or reflecting such a wave.

The assistance device may further comprise one or more of the following characteristics, taken alone or in combination.

The assistance device comprises a contact area intended to be in contact with the tank of the dispensing device when the user exerts an activation pressure on the tank to activate the dispensing of drops, the contact area comprising means for measuring the activation pressure exerted on the contact area in order to trigger the optical means and/or provide additional information on the amount of liquid product dispensed, preferably information on the magnitude of the activation pressure applied and the time during which this activation pressure is applied. The activation pressure exerted on the contact area measured by said means reflects the activation pressure exerted by the user on the tank, for example by a direct or indirect press on the assistance device, said press then being transmitted to the dispensing device or a direct or indirect press on the dispensing device by any suitable means. The information relating to the activation pressure exerted on the contact area may in fact be particularly useful. In particular, triggering the optical means only once the user has exerted a certain activation pressure reduces their energy consumption, extends their lifetime and avoids generating unnecessary information when the devices are not being used. Furthermore, in addition to the inclination of the dispensing device, the activation pressure exerted by the user has also been found to be a parameter affecting the volume of a dispensed drop. Thus, by measuring this activation pressure, the information processing system can make an additional and/or more precise estimation of the amount of liquid product dispensed and preferably also of the amount of liquid product remaining in the tank of the dispensing device.

"Means for measuring the activation pressure" generally refers to any means for directly measuring a pressure or a force.

The assistance device comprises means for measuring the weight of the dispensing device connected to the assistance device, configured to provide information on the amount of liquid in the tank. Using the information on the amount of liquid in the tank before and after use, the amount of product dispensed can be deduced. This information can be added to that obtained from other detection means, for example information on the inclination of the dispensing device, to obtain a more precise estimation of the volume of the dispensed drop and/or be compared therewith to check the results (amount of liquid product dispensed, amount of liquid product remaining) output by the information processing system. Advantageously, the means for measuring the weight comprise a weight sensor, for example of the Force Sensing Resistor (FSR) type, which can be arranged under the tank when the dispensing device is at rest and/or above the latter at rest. An example of a suitable weight sensor is the force sensing resistor manufactured by Flexiforce capable of measuring forces within the range 0 to 4 N. Advantageously, the means for measuring the weight comprise several weight sensors arranged around the tank to measure the weight of the dispensing device connected to the assistance device, regardless of its inclination.

The optical means comprise a transmitter and a receiver of an optical signal, configured to detect the presence of a drop disturbing the optical signal and to measure the duration of this presence. The optical signal is for example an infrared ray. The transmitter and the receiver can be arranged on each side of the dispensing orifice when the assistance device is connected to the dispensing device, such that each dispensed drop crosses the path of the optical signal. Optionally, the transmitter and the receiver are arranged on the same side of the dispensing orifice when the assistance device is connected to the dispensing device, the optical signal being received by reflection on a wall which is at least partially reflective. One example of a suitable infrared detector is a detector manufactured by OSRAM Opto Semiconductors Inc. or Vishay Semiconductor Opto Division. Advantageously, the optical means comprise a second transmitter and a second receiver of an optical signal, configured to validate the information on the dispensing of a drop of the liquid product by the dispensing device. This second transmitter and this second receiver are used to confirm that the disturbance of the first optical signal is in fact due to the formation and then detachment of a drop of liquid product.

The means for measuring the inclination comprise an inclinometer. The latter is, for example, an electronic gyroscope or an accelerometer whose performance is chosen according to requirements.

The information processing system comprises means for reading information shown on the dispensing device. The processing system can then access various pieces of information on the liquid product contained in the dispensing device or on the dispensing device itself, limiting or eliminating the need for manual configuration of the assistance device to adapt the dispensing to the features of the product to be dispensed and/or to the dispensing device. These pieces of information are for example the number of theoretical doses contained in the tank, the theoretical volume of a drop, the physical or chemical properties of the liquid product such as the viscosity, the technical characteristics of the dispensing device such as the valve dimensions, these characteristics and properties possibly being based on tables of predetermined values or calculation tools. Some of these pieces of information may be useful for processing information provided by the various means, for example the means for measuring the inclination. The dispensing device may comprise information media such as digital chips, magnetic tapes, bar codes, or any other type of medium storing information which can be read electronically.

The information processing system is connected to an object external to the assistance device, for example to a server, a receiver, an intranet or the internet. It can send, and possibly receive information remotely.

The assistance device comprises means for indicating the information provided by the processing system, for example visual means, audible means and/or tactile means. These means can be used to indicate to the user information on the correct dispensing of a dose, the amount of product dispensed and/or remaining and/or other information on the liquid product (for example read by the reading means). The display means may comprise a screen to display information alphanumerically and/or light signals, for example of different colour or shape.

The information processing system comprises means for storing a variable value corresponding to the amount of liquid product dispensed and/or the amount of liquid product remaining in the tank. The variable value is for example used to deduce the amount of liquid product dispensed and control the amount of liquid product remaining in the tank. The variable value concerning the amount of liquid product dispensed can also be used to check that the treatment is being respected. The variable value is updated when liquid is dispensed. Advantageously, the storage means can store other values and information useful for the processing system and/or the user.

The invention further relates to a kit for dispensing a liquid product in the form of drops on an organ of a subject, comprising a device for dispensing liquid product and an assistance device as described previously. The organ is for example an eye, an ear or the skin. Preferably, the assistance device and the dispensing device are separate devices, attached to each other and removable, but they could form a single unit and be made of the same material.

The invention further relates to a method for determining the amount of liquid product dispensed in the form of drops by a liquid dispensing device, by means of an assistance device as described above, comprising the following steps:
  detecting a drop,
  estimating the volume of the drop detected.

By applying the method throughout the time when the dispensing device is being used and adding the estimated volume of each drop detected and therefore dispensed, the total amount of liquid product dispensed during this use can be obtained.

A drop is detected by the optical means of the dispensing device. All the information provided by the optical means and the means for measuring the inclination is processed by the information processing system to estimate the volume of the drop detected and thus deduce the amount of liquid product dispensed.

The determination method may further comprise one or more of the following characteristics, taken alone or in combination.

The determination method comprises a step of calculating a new value of the residual volume by subtracting the volume of the drop detected from the previous value of the residual volume. The information processing system and/or the user therefore know the amount of liquid product remaining in the tank after dispensing the liquid product, this information not initially being accessible from outside the tank. Note that the first value corresponding to the "previous value of the residual volume" is the filling volume of the tank.

"Residual volume" generally means the volume of liquid product remaining in the tank of the dispensing device.

The step of detecting the drop comprises a step of identifying a disturbance of an optical signal provided by the optical means and a step of measuring the time during which the optical signal is disturbed. The disturbance may be, for example, the absence of an optical signal or a weak optical signal due to absorption of the optical signal by the presence of the drop in its path. A priori, the disturbance time would correspond to the time during which the drop is near the dispensing orifice.

The step of estimating the volume of the drop detected comprises a step of determining a theoretical volume of this drop, preferably comprising a step of calculating this theoretical volume using information on the viscosity of the liquid product and/or the geometric characteristics of the dispensing orifice, or even on other characteristics of the dispensing end piece and/or of the dispensing device. The theoretical volume is the volume calculated using fixed data on the liquid product or the dispensing device, which do not vary depending on the conditions of use of the dispensing device. The fixed data can be determined by the information processing system, for example after reading the information shown on the dispensing device, or directly by reading.

The step of estimating the volume of the drop comprises a step of weighting the volume of the drop detected, during which at least one of the following parameters is taken into account to weight the estimation of the volume of the drop detected:
  the magnitude of the activation pressure applied by the user on the tank to cause the formation of the drop,
  the variation profile of this activation pressure over time,
  the inclination of the assistance device and/or of the dispensing device,
  the time during which a signal provided by the optical means is disturbed,
  the measurement of the weight of the dispensing device.

By taking into account at least one of these parameters, the calculated theoretical volume is adjusted to the conditions of use of the dispensing device, in order to obtain a more realistic estimation and therefore a more precise and reliable determination of the amount of liquid product dispensed.

The determination method comprises a step of measuring the weight of the dispensing device to validate the calculated value of residual volume. Knowing the value of the residual volume obtained by measuring the weight, the amount of liquid product dispensed can be deduced. Thus, the weight measurement can also be used to validate the estimated volume of the drop detected. The step of measuring the weight can be triggered conditionally depending on the inclination detected, in particular depending on a predetermined period of time during which the dispensing device is kept inclined.

The determination method comprises a step of testing the presence of a protective cap on the dispensing device. Putting back the cap is advantageous to protect the dispensing device or to improve hygiene and the antimicrobial function if a residual amount of liquid product remains in the dispensing orifice. This test is performed to determine whether the cap has been put back after use and possibly to inform the user otherwise. Furthermore, when the determination method comprises a step of measuring the weight of the dispensing device, the presence or absence of the cap affects the value of the weight measured and must therefore be taken into account when determining the residual volume.

The step of detecting a drop is triggered by detection of an activation pressure by a user on the tank of the dispensing device to activate the dispensing of drops. To activate the dispensing of drops, in fact, the user must exert an activation pressure on the tank. Detection of this activation pressure indicates the start of a use and is a suitable time to trigger the drop detection step without the risk of omitting the detection of a drop. Detection of this activation pressure may be:
  direct, by measuring the pressure applied by the user on the bearing area to activate the dispensing device, or
  indirect, for example by measuring the pressure exerted on the contact area intended to be in contact with the tank of the dispensing device during the activation pressure by the user on the tank or on another bearing area.

BRIEF DESCRIPTION OF THE DRAWINGS

We will now describe particular embodiments of the invention given as non-limiting examples referring to the attached figures, on which:

FIG. 10 is a graph showing the steps of a method for determining the amount of liquid product dispensed by the liquid dispensing device of FIG. 1B, FIG. 11 is a set of a graph showing information processed by the assistance device of FIG. 1B and three longitudinal cross-sectional views of the upper part of the dispensing device of FIG. 1B at various steps while dispensing a drop, FIGS. 12 and 13 are two graphs showing the steps of a method for determining the amount of liquid product dispensed according to two other embodiments.

DETAILED DESCRIPTION OF THE INVENTION

Figure 1A:
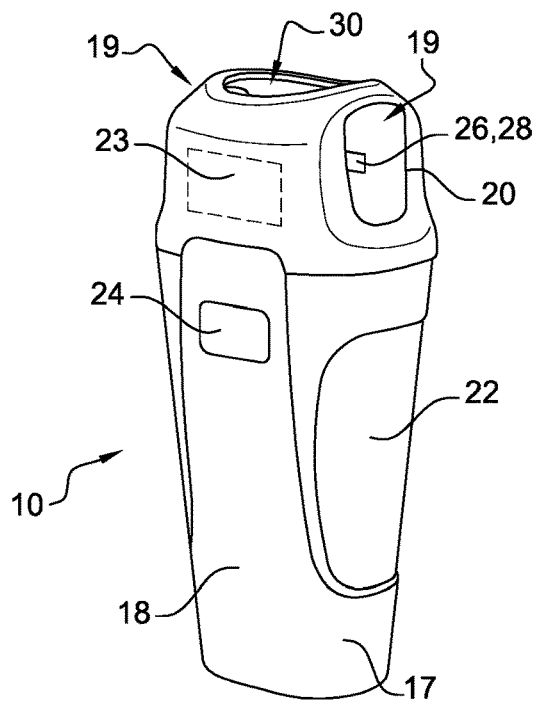
FIGS. 1A and 1B are perspective views of an assistance device according to one embodiment, FIG. 1A representing the assistance device alone and FIG. 1B representing the upper part of the assembly of the assistance device and of a dispensing device connected to the assistance device, the assistance device being in the open position and the dispensing device being provided with a cap for protecting the dispensing orifice.
Figure 1B:
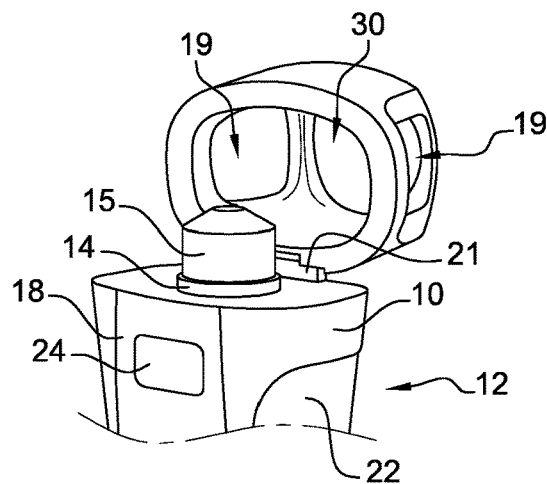

FIG. 1A Illustrates a device 10 for assisting with the use of a device for dispensing a liquid product in the form of drops and, FIG. 1B illustrates a dispensing kit 12 comprising the assistance device 10 and a dispensing device 14 arranged inside the assistance device 10. The dispensing device 14 comprises in this case a tank 32 (shown on FIG. 3) and a dispensing end piece provided with an orifice 16 for dispensing drops (shown on FIG. 2B) protected by a cap 15, for example screwed onto the dispensing end piece. The assistance device 10 comprises means 17 for connecting to the dispensing device 14 so that the dispensing kit 12 forms an integral assembly. The connection means 17 may comprise, for example, means for clipping the tank 32 into the assistance device 10. In a particular variant, the dispensing end piece provided with the dispensing orifice 16 could form part of the assistance device 10, attached to the tank 32 of the dispensing device 14 when connecting the assistance device 10 and the dispensing device 14.

The assistance device 10 comprises a main body 18 in which the dispensing device 14 is placed, and a bearing structure 20 to be pressed against the user's skin when dispensing drops into a target organ, for example an eye. The bearing structure 20 is removably mounted on the main body 18 between an open position for inserting the dispensing device 14 and a closed use position, for example by means of a hinge 21. The bearing structure 20 can be designed to be flexible enough to rest comfortably against the user's skin and adapt to the different reliefs near the target organ, and/or rigid enough to provide support when pressing and impose a predetermined distance between the dispensing orifice 16 and the target organ. The bearing structure 20 comprises an axial orifice 30 intended to allow drops of liquid product to fall from the dispensing orifice 16 towards the user's organ. The bearing structure 20 optionally comprises recesses 19 on two opposite sides and at its end, in particular to prevent the user's eye from being in the dark when the assistance device 10 is applied against the user's skin around the eye. The bearing structure 20 may have a contour that is closed or not, for example a C-shaped contour. The C-shaped contour allows, for example, the user to pull the lower eyelid through the opening of the C to open the eye wider and ensure that the drop reaches the eye.

The assistance device 10 also comprises a bearing area 22 intended in this case to allow the user both to grip and to press in order to dispense the liquid product. In this case, the bearing area 22 is arranged on two opposite sides of the main body 18. In another embodiment, a single bearing area could be arranged on only one side of the main body 18. An activation pressure exerted on the bearing area 22 is transmitted to the tank 32 of the dispensing device 14, in particular at a contact area 29 between the tank and the assistance device 10. The bearing area 22 may be made from a different material, in particular more flexible than that of the rest of the main body 18. It may also comprise reliefs to facilitate gripping by the user. Furthermore, due to the presence of the bearing area 22, the assistance device 10 increases the user's gripping area and the activation pressure area on the tank 32 compared with that of the dispensing device 14 alone, which is particularly advantageous for users with neuromuscular diseases.

The assistance device 10 further comprises means for measuring the inclination, configured to provide information on the inclination of the dispensing device 14 connected to the assistance device 10. In one example, the means for measuring the inclination comprise an inclinometer such as an electronic gyroscope or an accelerometer. The inclinometer is preferably placed in the main body 18, for example in an area intended to be placed near the dispensing end piece.

The assistance device 10 comprises an information processing system 23, in particular for processing information on the dispensing of a drop and on the inclination of the dispensing device 14 connected to the assistance device 10 in order to provide information on the amount of liquid product dispensed. The information processing system 23 is a system comprising a set of components (mechanical, electronic, chemical, photonic and/or biological) capable of processing information automatically. It comprises, for example, a printed circuit board (PCB), a set of transistors and/or a computer.

Advantageously, the assistance device 10 comprises an integrated energy source, for example a portable battery, for powering the various components, in particular the means for measuring the inclination and the information processing system 23. Alternatively, it is supplied with energy by an external power source.

Figure 6:
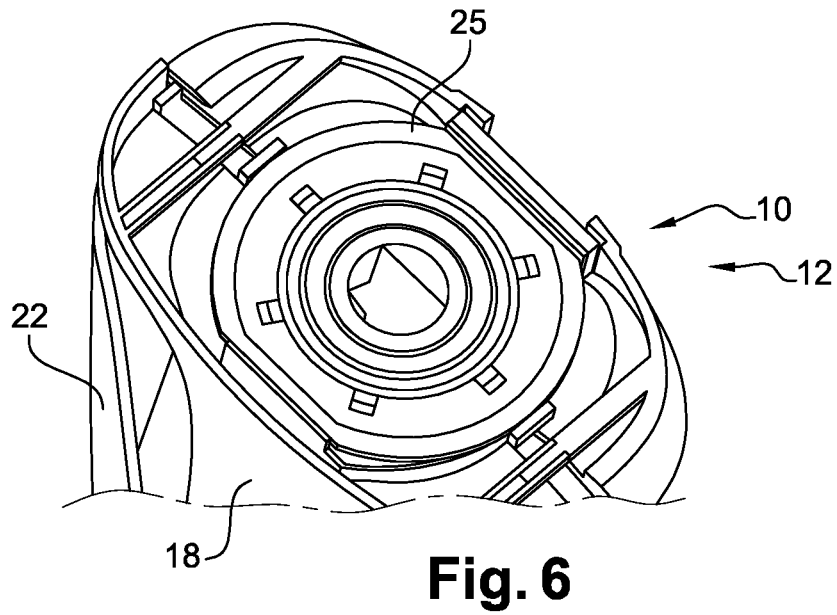
FIG. 6 is a top perspective view of the assistance device of FIG. 1A, without the upper part.
Figure 7:
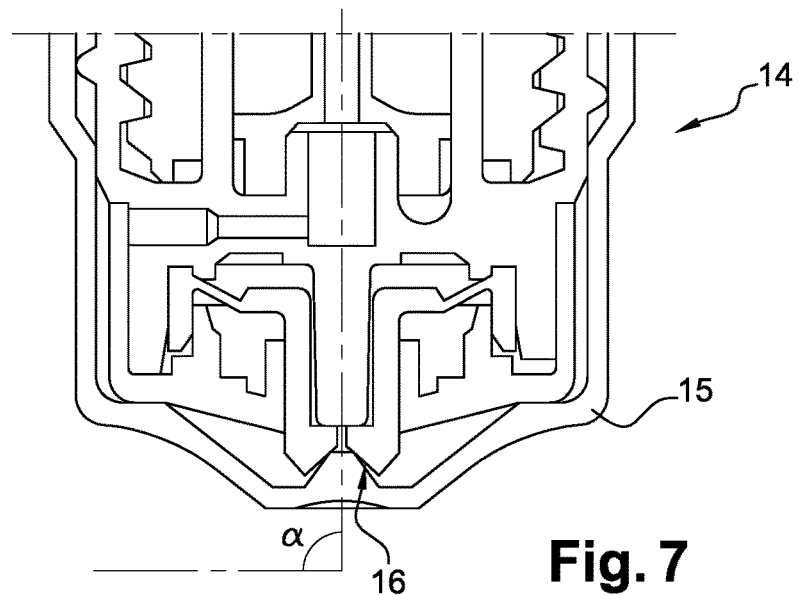
FIG. 7 is a longitudinal cross-sectional view of the upper part of the dispensing device of FIG. 1B.

The assistance device 10 advantageously comprises means for indicating the information provided by the processing system 23, for example visual means 24, 25, audible means and/or tactile means. In the embodiment of FIGS. 1A and 1B, it is provided with a screen 24 to display information alphanumerically. As shown on FIG. 6, the assistance device 10 further or alternatively comprises light-emitting diodes 25 around the dispensing orifice 16 to provide a light signal to indicate, for example, a correct inclination or a correct pressing force.

Figure 2A:
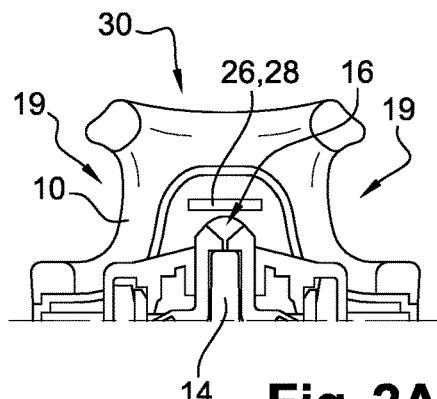
FIGS. 2A, 2B, 3 and 4 are schematic longitudinal cross-sectional views and in perspective for FIG. 3, of different parts of the assembly of FIG. 1B.
Figure 2B:
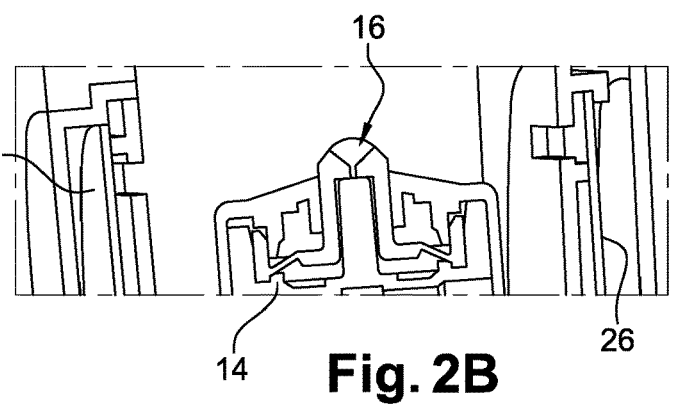

As illustrated on FIG. 2B, the assistance device 10 comprises optical means 26, 28 intended to be arranged near the dispensing orifice 16, and configured to provide information on the dispensing of a drop of the liquid product by the dispensing device 14. In this case, the optical means 26, 28 comprise a transmitter 26 and a receiver 28 of an optical signal 40, configured to detect the presence of a drop disturbing the optical signal 40 and to measure the duration of this presence. The transmitter 26 comprises, for example, infrared-emitting diodes and the receiver 28 comprises for example phototransistors capable of detecting infrared rays. The transmitter 26 and the receiver 28 detect the presence of a drop passing through the optical signal 40 when the optical rays are disturbed, for example by a variation in the intensity of the rays. The transmitter 26 and the receiver 28 are preferably located at a distance of between 1 and 3 mm, preferably 2 mm, from the dispensing orifice 16.

With a receiver of limited dimensions, when the assistance device is inclined, the passage of a drop may not be detected by this receiver. To overcome this problem, the receiver may advantageously have a reception area extending axially and/or circumferentially and guaranteeing that the passage of a drop is detected even when the assistance device is inclined.

Figure 3:
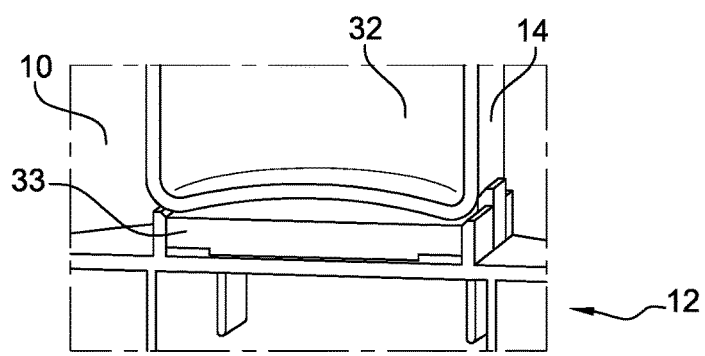

As shown on FIG. 3, the assistance device 10 comprises means for measuring the weight 33 of the dispensing device 14 connected to the assistance device 10, configured to provide information on the amount of liquid in the tank 32. The means for measuring the weight comprise a weight sensor, for example of the Force Sensing Resistor (FSR) type, arranged under the tank 32 to weigh the dispensing device 14 and deduce the weight, and therefore the volume, of the amount of liquid remaining in the tank 32. In a variant, not shown, the weight sensor is located above the tank. In another variant, not shown, the assistance device comprises several weight sensors arranged around the tank to measure the weight of the dispensing device connected to the assistance device, regardless of its inclination.

According to an embodiment, not shown, the assistance device may comprise means for detecting the dispensing device connected to the assistance device, for example a force-sensing resistor or an optical sensor, the information processing system being able to confirm to the user the presence of a dispensing device and/or to inform the user of the absence of a dispensing device.

The assistance device 10 and the dispensing device 14 may comprise blocking means to prevent the dispensing device 14 from rotating relative to the assistance device 10. The blocking means are particularly useful when the tank 32 is cylindrical. The blocking means may comprise complementary engagement shapes provided respectively on the assistance device 10 and on the dispensing device 14, for example a lug housed in a notch. Rotation being thus prevented, the user can screw the cap back on the dispensing end piece without the latter rotating freely. In addition, these blocking means, unlike a tight fit between the assistance device and the dispensing device, do not prevent the measurement of the weight of the dispensing device 14.

Figure 4:
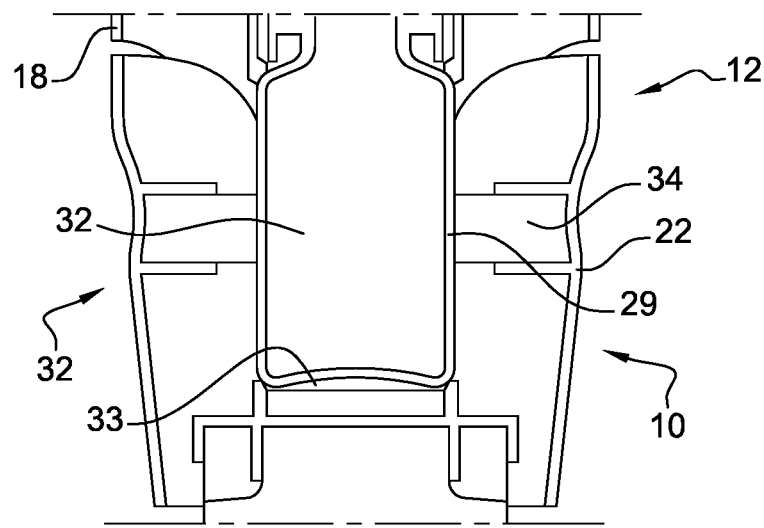

As shown on FIG. 4, the contact area 29 between the tank 32 and the bearing area 22 of the assistance device 10 comprises means for measuring the activation pressure exerted on the contact area 29 in order to trigger the optical means 26, 28 and/or provide additional information on the amount of liquid product dispensed. The means 34 for measuring the activation pressure may provide information on the magnitude of the activation pressure applied on the contact area 29 and the time during which this activation pressure is applied. The contact area 29 is located on an inner surface of the wall of the main body 18 carrying the bearing area 22. The means for measuring the activation pressure comprise, for example, a force-sensing resistor (FSR) 34, placed in contact with the tank 32.

Figure 5:
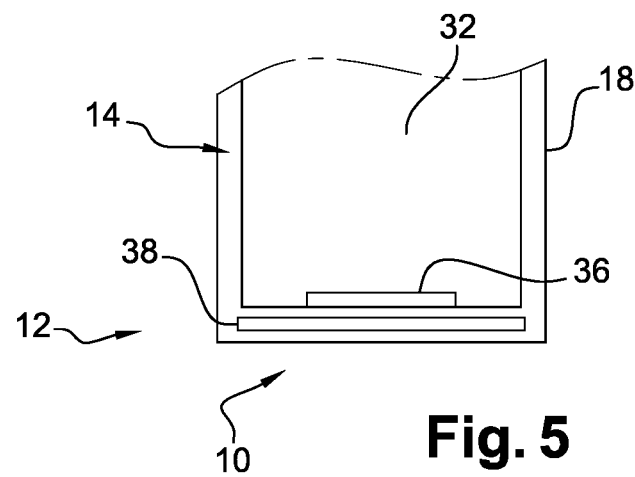
FIG. 5 is a schematic view of a part of an assembly of an assistance device and a dispensing device according to another embodiment.

As shown on the embodiment of FIG. 5, also applicable to the embodiment of FIG. 1A, the assistance device 10 comprises means for reading information 38 shown on the dispensing device 14. The dispensing device 14 comprises an information medium 36 which can be read electronically. This information medium is, for example, a radio tag 36 (such as an RFID (radio frequency identification) tag) affixed under the tank 32. The radio tag 36 comprises information such as, in this example, the filling volume of the tank 32 (and/or converted into a theoretical number of drops), the diameter of the dispensing orifice 16, the viscosity of the liquid product, the dosage of the liquid product, the expiry/manufacturing date. The reading means comprise, in this example, an antenna 38 capable of reading the radio tag 36 to extract the information required to process the information. The tag may also be affixed to the side of the tank or to any other suitable position.

In a variant, the information processing system 23 is connected to an object external to the assistance device 10, for example to a server, a receiver, an intranet or the internet.

Advantageously, the information processing system 23 comprises means 39 for storing a variable value on the amount of liquid product remaining in the tank 32.

We will now describe the method for determining the amount of liquid product dispensed in the form of drops by the liquid dispensing device 14, by means of the assistance device 10.

To determine the amount of liquid product dispensed, the presence of a drop near the dispensing orifice 16 is first detected using the optical means 26, 28, which trigger the measurement of the inclination of the assistance device 10. The information detected by the optical means 26, 28 and the means for measuring the inclination is then sent to the information processing system 23 which analyses it to provide an estimation of the volume of the drop detected. In another embodiment, the variation in the inclination of the assistance device 10 is first detected before triggering the optical means 26, 28. Knowing the inclination of the assistance device 10 and the geometry of the assistance device 10 and of the dispensing device 14, the inclination of the dispensing device 14 is known. By applying this method for determining the presence of a drop when using the dispensing device 14, a value representative of the amount of liquid product dispensed drop by drop can be obtained. Using this value, a new value of the residual volume can be calculated by subtracting the estimated volume of the drop detected or the amount of liquid product dispensed from the previous value of the residual volume of liquid product remaining in the tank 32. During a first use, the previous value of the residual volume is the filling volume of the tank 32. The value of the residual volume is a variable updated after dispensing a drop or after a use (several drops dispensed) and can be stored in the storage means of the assistance device 10.

Preferably, the presence of a drop is detected by identifying a disturbance of the optical signal 40 provided by the optical means 26, 28, said disturbance being generated by the presence of a drop passing through the optical signal 40 between the transmitter 26 and the receiver 28, and more preferably, by also measuring the time during which the optical signal 40 is disturbed.

The volume of the drop detected can be estimated in two steps. A first step consists in determining a theoretical volume of the drop, for example by using information on the viscosity of the liquid product and/or the geometric characteristics of the dispensing orifice 16, or even on other characteristics of the dispensing end piece. A method for determining the theoretical volume of a drop consists in taking as a value the volume of a drop when the dispensing device 14 is inclined at an angle α (alpha) of 90° from the horizontal, taking into account the diameter of the dispensing orifice 16 and the viscosity of the liquid product, two fixed parameters which have a significant impact on the volume of a dispensed drop. A "fixed parameter" means a parameter which does not depend on the conditions of use of the assistance device 10, such as the inclination, the activation pressure, the pressing speed, etc. This information is for example read by the assistance device 14 on a radio tag 36 of the dispensing device 14. In addition, we understand that the angle of inclination a corresponds to the angle formed by the axis of the dispensing device 14, corresponding to the axis of the dispensing orifice 16, relative to a horizontal direction, in reference to the direction of gravity which defines a vertical direction.

Figure 8:
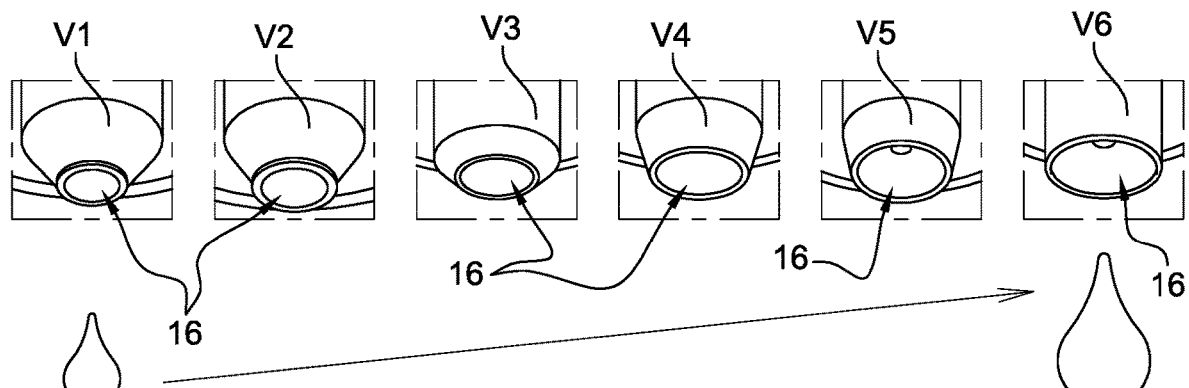
FIG. 8 is a perspective view of various orifices for dispensing liquid product in the form of drops.

As shown on FIG. 8 which illustrates six dispensing valves V1 to V6 of a dispensing device 14 having different shapes and dimensions, we see that, generally, the volume of a drop increases with the diameter of the dispensing orifice 16. The table below is an example showing the relation between the diameter of the dispensing orifice 16 and the theoretical volume of the drop. The results were obtained with water, inclining the dispensing device 14 through an angle α of 90°.

|  | Valve and dimension of the orifice (in mm) | | | | | |
| --- | --- | --- | --- | --- | --- | --- |
|  | V1: 1.6 | V2: 2.0 | V3: 2.4 | V4: 2.7 | V5: 3.0 | V6: 3.6 |
| Theoretical volume of the drop (in µL) | 28 | 33 | 40 | 43 | 46 | 53 |

Furthermore, we see that the viscosity of the liquid product affects the volume of a dispensed drop, even without taking into account variable parameters depending on the conditions of use of the dispensing device 14. Thus, we see that the volume of a drop under theoretical conditions of use (dispensing device 14 inclined at an angle α of 90° from the horizontal with the valve V3) increases with the viscosity of the liquid product. The table below is an example showing the relation between the viscosity of the liquid product and the theoretical volume of the drop.

| Viscosity (in cP) | 0 | 50 | 200 | 1000 |
|---|---|---|---|---|
| Theoretical volume of the drop (in μL) | 40 | 41 | 42 | 50 |

A second step consists in weighting the theoretical volume by taking into account at least one of the following parameters:
- the magnitude of the activation pressure applied by the user on the tank 32 to cause the formation of the drop,
- the variation profile of this activation pressure over time,
- the inclination of the assistance device 10 and of the dispensing device 14,
- the time during which an optical signal 40 provided by the optical means is disturbed,
- the measurement of the weight of the dispensing device 14.

A method for weighting the theoretical volume consists, for example, in multiplying its value by a coefficient A1 related to the inclination of the assistance device 10 and of the dispensing device 14 provided by the means for measuring the inclination and by a coefficient A2 related to the time during which an optical signal 40 provided by the optical means 26, 28 is disturbed and to the viscosity of the liquid product contained in the tank 32.

Figure 9:
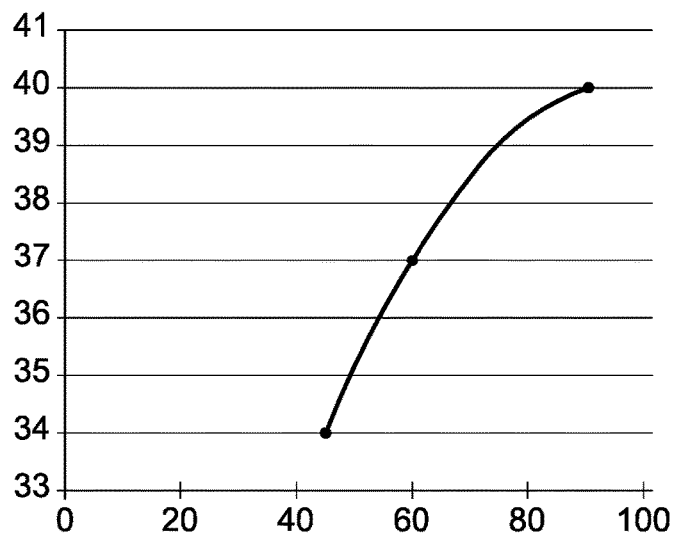
FIG. 9 is a graph showing the change in volume of a drop depending on the inclination of the dispensing device while dispensing liquid product.

Thus, we see that the inclination of the dispensing device 14 while dispensing a drop affects the volume of this drop. As shown on the graph of FIG. 9, the volume of the dispensed drop (y-axis) increases with the angle of inclination a of the dispensing device 14 (x-axis) measured from the horizontal. For example, a volume of 34 μL is measured at an inclination angle α of 45°, a volume of 37 μL at an inclination angle α of 60° and a volume of 40 μL at an inclination angle α of 90°, the liquid product used being water and the valve used being the valve V3 used as reference. After receiving the value of the inclination provided by the means for measuring the inclination, the information processing system 23 calculates the coefficient A1 by dividing this value of the inclination by the theoretical volume of a water drop when the dispensing device 14 is inclined at an angle α of 90° from the horizontal by taking the valve V3, i.e. 40 μL.

Furthermore, we see that the volume of the dispensed drop may vary with the viscosity of the liquid product depending on the speed of formation of the drop. It is therefore also interesting to weight the theoretical volume of a drop by a coefficient A2 taking into account the viscosity of the liquid product and the speed of formation of the drop. This speed of formation of the drop is advantageously obtained using the time during which the optical signal 40 is disturbed and/or the magnitude and duration of the activation pressure exerted to dispense a drop. The table below gives an example showing the relation between an assembly formed by the viscosity of the liquid product and the speed of formation of the drop, and the coefficient A2.

| Speed (in s) | Viscosity (in cP) | | | | |
|---|---|---|---|---|---|
| | 0 | 50 | 200 | 1000 | |
| <1 s | 0.75 | 0.80 | 1.07 | 1.20 | A2 |
| >2 s | 0.75 | 1.00 | 1.00 | 1.00 | |

In a variant, the theoretical volume of a drop may also be weighted by a coefficient related to the magnitude of the activation pressure applied by the user on the tank 32 to cause the formation of the drop and/or the variation profile of this activation pressure over time.

FIG. 10 describes an example of the steps of a determination method. The method starts with a first step E1 of detecting an activation pressure exerted by the user on the bearing area 22, said pressure being transmitted to the tank 32 of the dispensing device 14 via the contact area 29 between the dispensing device 14 and the assistance device 10 where an activation pressure sensor is arranged. When the activation pressure detected exceeds a predetermined threshold, for example 15 N, the optical means 26, 28 and the means for measuring the inclination are then switched on to detect a drop and measure the inclination of the dispensing device 14 in a step E2. The optical means 26, 28 monitor the area where the drop is formed near the dispensing orifice 16 until they detect the presence of a drop (step E3). A time counter is started at step E4 when the drop is detected. The time is counted until the drop leaves the formation area monitored by the optical means, i.e. until the drop detaches from the dispensing orifice 16. Once the drop has left the formation area in order to be dispensed (step E5), the optical signal 40 of the optical means 26, 28 is modified, more precisely the optical signal 40 is no longer disturbed, and the time counter stops in order to provide a drop formation time to the information processing system 23 which increments by one unit the number of drops dispensed (step E6). The means for measuring the inclination provide the inclination measurements to the information processing system 23 to estimate the volume of the drop (step E6). In an optional step E7, the residual volume as well as the number of drops remaining in the tank 32 can be deduced. This method can be repeated several times as long as an activation pressure exceeding the predetermined threshold is detected and/or the optical means 26, 28 detect the presence of a drop.

FIG. 11 shows a graph with the time on the x-axis and the magnitude of the activation pressure and the intensity of the disturbance of the optical signal 40 on the y-axis. The graph is an example of a representation of the information that the information processing system 23 receives from the optical means 26, 28 (curve C1) and from the means for measuring the activation pressure 34 (curve C2) exerted by the user while dispensing a drop. When the measured activation pressure exceeds a predetermined threshold, for example 15 N, the optical means 26, 28, in this case the transmitter 26 and the receiver 28 of an optical signal 40, are switched on. When a drop forms between the transmitter 26 and the receiver 28, the optical signal 40 is disturbed, which generates a high intensity of the disturbance. This disturbance disappears once the drop detaches from the dispensing orifice 16.

Another example of a determination method is shown on FIG. 12, used to check the value of the residual volume calculated in step E7 of the example of FIG. 10 by measuring the weight of the dispensing device 14. Steps E1 To E7 are similar to those of the example of FIG. 10 and are not described. After calculating the residual volume in step E7, the means for measuring the inclination continue to provide data to the information processing system 23. The information processing system performs a step E8 of testing the vertical position. Once the dispensing device 14 and/or the assistance device 10 have returned to their rest positions, the information processing system 23 validates the vertical position and a step E9 of measuring the weight of the dispensing device 14 is performed by suitable means of the assistance device 10. In a variant, step E8 is not performed, in other words the weight of the dispensing device 14 is measured regardless of the inclination of the dispensing device 14 and/or of the assistance device 10, for example after a large variation in the inclination of the dispensing device 14 after dispensing drops. The weight measured in step E9 varies depending on whether or not the cap 15 is present on the dispensing device 14. A step E10 is therefore performed to check whether the cap 15 has been put back. This check is either carried out manually by the user who provides this information to the assistance device 10, or more advantageously by means for detecting the cap 15 located on the assistance device 10. The means for detecting the cap 15 may comprise, for example, a mechanical contact or activation pressure sensor, or more advantageously the optical means. Thus, depending on the type of disturbance of the optical signal 40, the information processing system 23 and/or the optical means 26, 28 may determine whether a drop of liquid or a cap 15 is present. Depending on the result obtained in step E10, the information processing system 23 uses the weight measured to calculate, in a step E11, the amount of liquid remaining in the tank 32.

FIG. 13 shows a variant of the embodiment of FIG. 12. In this variant, the step E10 of checking whether the cap 15 has been put back is carried out solely by the information processing system 23 with data which is calculated, pre-configured and/or read on the dispensing device 14. This step E10' comprises two successive sub-steps E10'a and E10'b. In step E10'a, the information processing system 23 estimates the weight of the dispensing device 14 with (respectively without) cap 15 by adding the weight of the residual volume (obtained in step E6) and the empty weight of the dispensing device 14 with (respectively without) cap 15. In step E10'b, the information processing system 23 compares the measured weight with the estimated weight of the dispensing device 14 with (respectively without) cap 15. If the measured weight is much less than the estimated weight of the dispensing device 14 with cap 15 and/or approximately equal to the estimated weight of the dispensing device 14 without cap 15, then the information processing system 23 deduces that the cap 15 has not been put back on the dispensing device 14. If the measured weight is much greater than the estimated weight of the dispensing device 14 without cap 15 and/or approximately equal to the estimated weight of the dispensing device 14 with cap 15, then the system deduces that the cap 15 has been put back. Depending on the result obtained in step E10', the information processing system 23 calculates, in step E11, the amount of liquid remaining in the tank 32 by subtracting the empty weight of the dispensing device 14 with or without cap 15 from the measured weight.

According to an alternative embodiment, not shown, the activation pressure exerted by the user on the bearing area is determined using the means for measuring the weight of the dispensing device connected to the assistance device. With a flexible tank, the activation pressure deforms the tank radially along its diameter and also longitudinally along its length. The deformation along the length can be measured by the balance and the information on the activation pressure deduced. In this alternative embodiment, the contact area is separate from the user's bearing area.

The invention is not limited to the embodiments described and other embodiments will be clearly apparent to those skilled in the art. For example, the various means described may be combined to obtain an assistance device, a dispensing kit or a determination method adapted to the need.

The invention claimed is:

1. An assistance device for assisting with the use of a device for dispensing a liquid product in the form of drops and comprising a tank, the assistance device comprising:

a connector for rigid connection to the dispensing device,
an optical device configured to be arranged near an orifice for dispensing the liquid product and configured to provide information on the dispensing of a drop of the liquid product by the dispensing device, wherein the assistance device further comprises:
a measuring device for measuring the inclination configured to provide information on the inclination of the dispensing device connected to the assistance device, and
a system for processing information on the dispensing of a drop and on the inclination of the dispensing device connected to the assistance device in order to provide information on the amount of liquid product dispensed.

2. The assistance device according to claim 1, comprising a contact area intended to be in contact with the tank of the dispensing device when the user exerts an activation pressure on the tank to activate the dispensing of drops, the contact area comprising a measuring device for measuring the activation pressure exerted on the contact area in order to trigger the optical device and/or provide additional information on the amount of liquid product dispensed or both.

3. The assistance device according to claim 2 wherein the additional information on the amount of liquid product dispensed comprises information on the magnitude of the activation pressure applied, the time during which this activation pressure is applied or both.

4. The assistance device according to claim 1, comprising a measuring device for measuring the weight of the dispensing device connected to the assistance device, configured to provide information on the amount of liquid in the tank.

5. The assistance device according to claim 1, wherein the optical device comprises a transmitter and a receiver of an optical signal, configured to detect the presence of a drop disturbing the optical signal and to measure the duration of this presence.

6. The assistance device according to claim 1, wherein the measuring device for measuring the inclination is an inclinometer.

7. The assistance device according to claim 1, wherein the information processing system comprises a device for reading information shown on the dispensing device.

8. The assistance device according to claim 1, wherein the information processing system comprises a device for storing a variable value corresponding to the amount of liquid product dispensed, the amount of liquid product remaining in the tank or both.

9. A kit for dispensing a liquid product in the form of drops, comprising a device for dispensing a liquid product and an assistance device according to claim 1.

10. A method for determining the amount of liquid product dispensed in the form of drops by a liquid dispensing device with an assistance device according to claim 1, comprising the following steps:

detecting a drop, and
estimating the volume of the drop detected.

11. The method according to claim 10, wherein the step of detecting the drop comprises a step of identifying a disturbance of an optical signal provided by the optical device and a step of measuring the time during which the optical signal is disturbed.

12. The method according to claim 10, wherein the step of estimating the volume of the drop detected comprises a step of determining a theoretical volume of this drop.

13. The method according to claim 12, wherein the step of estimating the volume of the drop comprises a step of weighting the volume of the drop detected, during which at least one of the following parameters is taken into account to weight the estimation of the volume of the drop detected:
- the magnitude of the activation pressure applied by the user on the tank to cause the formation of the drop,
- the variation profile of this activation pressure over time,
- the inclination of the assistance device or of the dispensing device,
- the time during which an optical signal provided by the optical device is disturbed,
- the measurement of the weight of the dispensing device.

14. The method according to claim 12 wherein the theoretical volume of the drop is calculated using information on the viscosity of the liquid product, the geometric characteristics of the dispensing orifice, other characteristics of the dispensing end piece, other characteristics of the dispensing device or combinations thereof.

15. The method according to claim 10, comprising a step of calculating a new value of the residual volume by subtracting the volume of the drop detected from the previous value of the residual volume.

16. The method according to claim 15, comprising a step of measuring the weight of the dispensing device to validate the calculated value of residual volume.

17. The method according to claim 10, comprising a step of testing the presence of a protective cap on the dispensing device.

18. The method according to claim 10, during which the step of detecting a drop is triggered by the detection of an activation pressure made by a user on the tank of the dispensing device to activate the dispensing of drops.

* * * * *